United States Patent [19]

Raddatz et al.

[11] Patent Number: 5,288,733
[45] Date of Patent: Feb. 22, 1994

[54] QUINOLYLMETHOXYPHENYLACETIC ACID ACYLAMIDES AND UREAS

[75] Inventors: Siegfried Raddatz, Cologne; Klaus-Helmut Mohrs; Michael Matzke, both of Wuppertal; Romanis Fruchtmann, Cologne; Armin Hatzelmann, Konstanz; Reiner Muller-Peddinghaus, Bergisch Gladbach, all of Fed. Rep. of Germany

[73] Assignee: Bayer Aktiengesellschaft, Leverkusen, Fed. Rep. of Germany

[21] Appl. No.: 979,756

[22] Filed: Nov. 23, 1992

[30] Foreign Application Priority Data

Dec. 3, 1991 [DE] Fed. Rep. of Germany ....... 4139750

[51] Int. Cl.$^5$ .................... C07D 215/14; A61K 31/47
[52] U.S. Cl. .................................... 514/311; 546/174; 546/175
[58] Field of Search ................. 546/174, 175; 514/311

[56] References Cited

U.S. PATENT DOCUMENTS

| | | | |
|---|---|---|---|
| 4,970,215 | 11/1990 | Mohrs et al. | 514/311 |
| 5,091,392 | 2/1992 | Raddatz et al. | 546/176 |

FOREIGN PATENT DOCUMENTS

| | | |
|---|---|---|
| 0339416 | 11/1989 | European Pat. Off. . |
| 0344519 | 12/1989 | European Pat. Off. . |
| 0414019 | 2/1991 | European Pat. Off. . |
| 0428860 | 5/1991 | European Pat. Off. . |

OTHER PUBLICATIONS

Borgeat, P. et al., Proc. nat. Acad. Sci. 76, 2148–2152 (1979).
E. L. Eliel, Stereochemistry of Carbon Compounds, McGraw Hill, 1962.

Primary Examiner—David B. Springer
Attorney, Agent, or Firm—Sprung Horn Kramer & Woods

[57] ABSTRACT

Quinolylmethoxyphenylacetic acid acylamides and ureas can be prepared either by reacting corresponding carboxylic acids with amides or reacting corresponding amides with isocyanates or ureas. The quinolylmethoxyphenylacetic acid acylamides or ureas can be used as active compounds in medicaments.

8 Claims, No Drawings

QUINOLYLMETHOXYPHENYLACETIC ACID ACYLAMIDES AND UREAS

The invention relates to quinolylmethoxyphenylacetic acid acylamides and ureas, processes for their preparation and their use in medicaments.

Substituted 4-(quinolin-2-yl-methoxy)phenylacetic acid derivatives and α-unsubstituted 4-(quinolin-2-yl-methoxy)-phenylacetic acid derivatives are known from EP 344 519 (U.S. Pat. No. 4,970,215) and EP 339 416.

Moreover, substituted (quinolin-2-yl-methoxy)-phenylcarbonylureas are known from EP 428 860.

The present invention relates to quinolylmethoxyphenylacetic acid acylamides and ureas of the general formula (I)

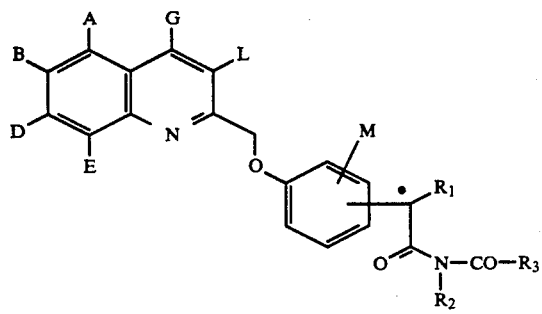

in which

A, B, D, E, G, L and M independently of one another represent hydrogen, hydroxyl, halogen, cyano, carboxyl, nitro, trifluoromethyl or trifluoromethoxy, or represent straight-chain or branched alkyl or alkoxy having in each case up to 8 carbon atoms, or represent aryl having 6 to 10 carbon atoms, which is optionally substituted by halogen, hydroxyl, nitro or cyano, $R^1$ represents cycloalkyl having 3 to 12 carbon atoms, which is optionally substituted by straight-chain or branched alkyl having up to 8 carbon atoms, $R^2$ represents hydrogen, straight-chain or branched alkyl having up to 6 carbon atoms or benzyl and $R^3$ represents straight-chain or branched alkyl having up to 8 carbon atoms, benzyl, cycloalkyl having 3 to 12 carbon atoms or phenyl, which is optionally substituted by halogen, nitro, cyano or hydroxyl, or represents a group of the formula —$NR^4R^5$, wherein $R^4$ and $R^5$ are identical or different and denote hydrogen, straight-chain or branched alkyl having up to 6 carbon atoms, benzyl or phenyl, if appropriate in an isomeric form, and salts thereof.

Surprisingly, the quinolylmethoxyphenylacetic acid acylamides and ureas of the general formula (I) according to the invention have a high in vitro activity as leukotriene synthesis inhibitors.

Physiologically acceptable salts are preferred in the context of the present invention. Physiologically acceptable salts of the quinolylmethoxyphenylacetic acid acylamides and ureas can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention moreover are salts of monovalent metals, such as alkali metals, and the ammonium salts. The sodium, potassium and ammonium salts are preferred.

The compounds according to the invention exist in stereoisomeric forms (*), which are either mirror images of one another (enantiomers), or are not mirror images of one another (diastereomers). The invention relates both to the antipodes and to the racemic forms, as well as to the diastereomer mixtures. Like the diastereomers, the racemic forms can be separated into the stereoisomerically uniform constituents in a known manner (compare E.L. Eliel, Stereochemistry of Carbon Compounds, McGraw Hill, 1962].

Preferred compounds of the general formula (I) are those in which

A, B, D, E, G, L and M independently of one another represent hydrogen, hydroxyl, fluorine, chlorine, bromine, carboxyl, nitro, trifluoromethyl or trifluoromethoxy, or represent straight-chain or branched alkyl or alkoxy having in each case up to 6 carbon atoms, or represent phenyl, which is optionally substituted by fluorine, chlorine, bromine, hydroxyl, nitro or cyano, $R^1$ represents cyclopropyl, cyclobutyl, cyclopentyl, cyclohexyl, cycloheptyl or -cyclooctyl, which are optionally substituted by straight-chain or branched alkyl having up to 6 carbon atoms, $R^2$ represents hydrogen or straight-chain or branched alkyl having up to 4 carbon atoms and $R^3$ represents straight-chain or branched alkyl having up to 6 carbon atoms, benzyl, cyclopropyl, cyclopentyl, cyclohexyl, cycloheptyl or phenyl, which is optionally substituted by fluorine, chlorine, bromine or hydroxyl, or represents a group of the formula —$NR^4R^5$, wherein $R^4$ and $R^5$ are identical or different and denote hydrogen, straight-chain or branched alkyl having up to 4 carbon atoms or benzyl, if appropriate in an isomeric form, and salts thereof.

Particularly preferred compounds of the general formula (I) are those in which

A, B, D, E, G, L and M independently of one another represent hydrogen, hydroxyl, fluorine, chlorine, bromine or straight-chain or branched alkyl having up to 4 carbon atoms, $R^1$ represents cyclopropyl, cyclopentyl, cyclohexyl or cycloheptyl, which are optionally substituted by straight-chain or branched alkyl having up to 4 carbon atoms, $R^2$ represents hydrogen, methyl, ethyl or phenyl and $R^3$ represents straight-chain or branched alkyl having up to 4 carbon atoms, cyclopropyl, cyclopentyl or cyclohexyl, or represents a group of the formula —$NR^4R^5$, wherein $R^4$ and $R^5$ are identical or different and denote hydrogen, methyl, ethyl or benzyl.

Especially preferred compounds of the general formula (I) are those in which A, B, D, E, G, L and M represent hydrogen.

Compounds which are also especially preferred are those in which the radical

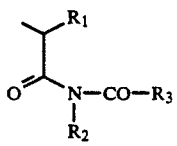

is in the 4-position relative to the quinolylmethoxy radical.

Furthermore, processes for the preparation of the compounds of the general formula (I) according to the invention have been found, characterised in that

[A] carboxylic acids of the general formula (II)

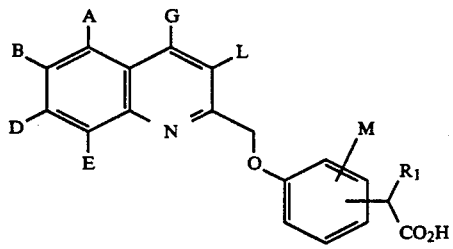

in which A, B, D, E, G, L, M and $R^1$ have the abovementioned meaning,
are reacted, if appropriate after activation of the carboxylic acid function, for example by way of the acid halides or anhydrides, with amides of the general formula (III)

$$H_2N-CO-R^3 \qquad (III)$$

in which $R^3$ has the abovementioned meaning,
in organic solvents, if appropriate in the presence of bases, or

[B] otherwise, in the case where $R^3$ represents the group $-NR^4R^5$, amides of the general formula (IV)

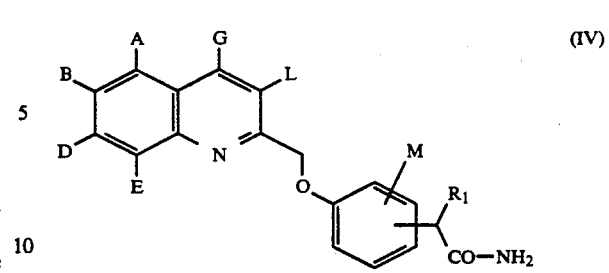

in which A, B, D, E, G, L, M and $R^1$ have the abovementioned meaning,
are subjected to a condensation reaction either with halogenosulphonylisocyanates of the general formula (V) or with ureas of the general formula (VI)

$$T-SO_2-N=C=O \text{ (V) or } H_2N-CO-NR^4R^5 \qquad (VI)$$

in which
$R^4$ and $R^5$ have the abovementioned meaning and
T represents halogen, preferably chlorine,
under the reaction conditions described under [A], or

[C] the compounds of the general formula (IV) are reacted with acetals of the general formula (VII)

in which
$R^3$ has the abovementioned meaning and
$R^6$, $R^7$, $R^8$ and $R^9$ are identical or different and denote $C_1$-$C_6$ alkyl,
in the presence of acetic acid, and in the case where $R^2$, $R^4$ and/or $R^5$ do not denote hydrogen, if appropriate an alkylation is also carried out subsequently, by customary methods, and the substituents A, B, D, E, G, L and M are likewise varied by known methods, and in the case of the enantiomerically pure compounds, the corresponding acids are separated by customary methods and then reacted further as described above.

The process according to the invention can be illustrated by way of example by the following equation:

[A]

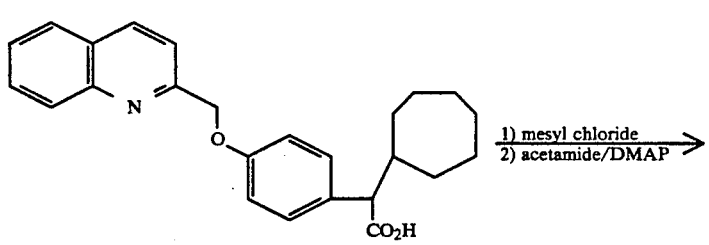

1) mesyl chloride
2) acetamide/DMAP

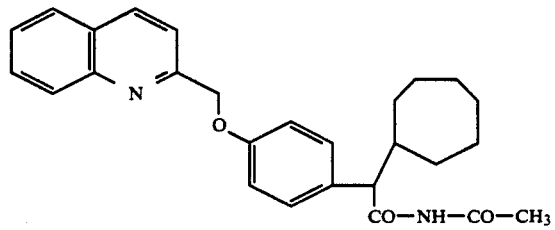

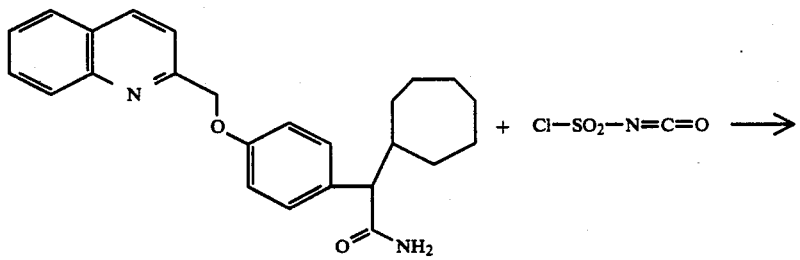

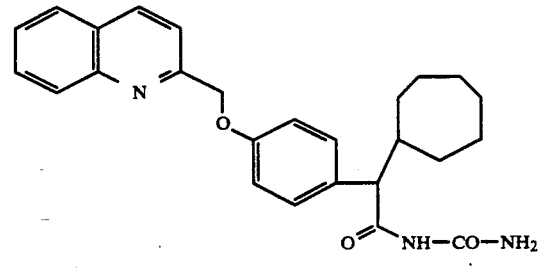

Suitable solvents here are inert organic solvents which do not change under the reaction conditions. These include ethers, such as diethyl ether or tetrahydrofuran, halogenohydrocarbons, such as dichloromethane, trichloromethane, tetrachloromethane, 1,2-dichloroethane, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Dichloromethane is particularly preferred. Tetrahydrofuran, acetone and dimethylformamide are preferred.

Suitable bases for the individual process steps, in particular for the amidation and acylation, are the customary basic compounds. These include, preferably, alkali metal hydroxides and alkaline earth metal hydroxides, such as lithium hydroxide, sodium hydroxide, potassium hydroxide or barium hydroxide, alkali metal hydrides, such as sodium hydride, alkali metal carbonates or alkaline earth metal carbonates, such as sodium carbonate or potassium carbonate, or alkali metal alcoholates, such as, for example, sodium methanolate or ethanolate, potassium methanolate or ethanolate or potassium tert-butylate, or organic amines, such as benzyltrimethylammonium hydroxide, dimethylaminopyridine, piperidine, tetrabutylammonium hydroxide, pyridine, triethylamine or N-methylpiperidine. Potassium carbonate, sodium hydride, piperidine, triethylamine and dimethylaminopyridone are preferred.

The amidation and acylation are in general carried out in a temperature range from 0° C. to 150° C., preferably at 25° C. to 100° C.

The amidation and acylation are in general carried out under normal pressure. However, it is also possible to carry out the process under reduced pressure or under increased pressure (for example in a range from 0.5 to 5 bar.

The customary reagents are suitable for activating the carboxylic acid, such as inorganic halides, for example thionyl chloride, mesyl chloride, phosphorus trichloride or phosphorus pentachloride, or carbonyldiimidazole, carbodiimides, such as cyclohexylcarbodiimide or 1-cyclohexyl-3-[2-(N-methylmorpholino)ethyl]carbodiimide p-toluenesulphonate, or N-hydroxyphthalimide or N-hydroxybenzotriazole.

Suitable solvents for the alkylation are likewise the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the solvents mentioned. Dichloromethane is preferred.

In general, 1 to 3 mol, preferably 1 to 2 mol, particularly preferably 1 mol, of halogenosulphonyl isocyanate are employed per mol of the amide.

The compounds of the general formula (II) are known per se or can be prepared by a customary method (compare German Offenlegungsschrift 3,818,443].

The compounds of the general formula (III) are known or can be prepared by customary methods (compare CA I 60-35-5].

The halogenosulphonyl isocyanates of the general formula (V) are likewise known.

The ureas of the general formula (VI) are likewise known. The compounds of the general formula (IV) are new and can be prepared by amidating the acids of the general formula (II) , likewise after activation of the carboxylic acid function as described above with one of the solvents mentioned above, either in a stream of ammonia or by reaction with the corresponding amines, or by reducing the corresponding 2-alkylated 2-[4-(quinolin-2-yl-methoxy)phenyl]acetonitriles with acids, for example hydrochloric acid.

The process is in general carried out in a temperature range from −10° C. to 120° C., preferably from 25° C. to 100° C., under normal pressure.

The compounds of the general formula VII are known per se (compare Beil. 4, 308).

The compounds according to the invention can be employed as active compounds in medicoments. The substances can act as inhibitors of enzymatic reactions in the context of arachidonic acid metabolism, in particular of 5-lipoxygenase.

Surprisingly, the compounds of the general formula (I) exhibit a high in vitro activity as leukotriene synthesis inhibitors and a potent in vivo action following -oral administration.

They are thus preferably suitable for the treatment and prevention of diseases of the respiratory passages, such as allergies/asthma, bronchitis, emphysema, shock lung, pulmonary hypertension, inflammations/rheumatism and oedemas, thromboses and thromboembolisms, ischaemias (disturbances in peripheral, cardiac and cerebral blood flow), cardiac and cerebral infarctions, disturbances in cardiac rhythm, angina pectoris, arteriosclerosis, in tissue transplant cases, dermatoses, such as psoriasis, inflammatory dermatoses, for example eczema, dermatophyte infection, infections of the skin by bacteria and metastases, and for cytoprotection in the gastrointestinal tract.

The compounds according to the invention can be used both in human medicine and in veterinary medicine.

The pharmacological action data of the substances according to the invention are determined by the following method:

The release of leukotriene $B_4$ ($LTB_4$) on polymorphonuclear human leucocytes (PMN) after addition of the substances and Ca ionophore was determined in vitro by means of reverse phase HPLC by the method of Borgeat, P. et al., Proc. Nat. Acad. Sci. 76, 2148-2152 (1979), as a measure of the 5-lipoxygenase inhibition.

The present invention also includes pharmaceutical formulations which, in addition to inert, non-toxic, pharmaceutically suitable auxiliaries and excipients, comprise one or more compounds of the general formula (I), or which consist of one or more active compounds of the formula (I), and processes for the preparation of these formulations.

The active compounds of the formula (I) should be present in these formulations in a concentration of 0.1 to 99.5% by weight, preferably 0.5 to 95% by weight of the total mixture.

In addition to the active compounds of the formula (I), the pharmaceutical formulations can also comprise other pharmaceutical active compounds.

The abovementioned pharmaceutical formulations can be prepared in a customary manner by known methods, for example with the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, in order to achieve the desired result.

However, where appropriate, it may be advantageous to deviate from the amounts mentioned, and in particular to do so as a function of the nature and body weight of the subject to be treated, of the behaviour of the individual towards the medicament, of the nature and severity of the disease, of the nature of the formulation and administration, and of the time or interval at which administration takes place.

Starting compounds

Example I

2-[4-(Quinolin-2-yl-methoxy)phenyl]-acetonitrile

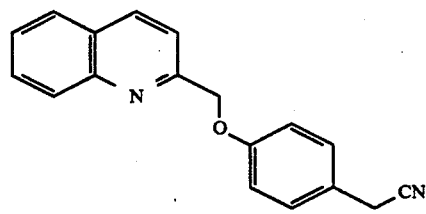

18 g (0.101 mol) of quinoline-2-methyl chloride, 13.3 g (0.1 mol) of 4-hydroxyphenylacetonitrile and 14 g (0.1 mol) of potassium carbonate (powdered and dried at 110° C.) are heated at the boiling point in 400 ml of dry acetone for 72 hours. The mixture is then allowed to cool, the solid product is filtered off and the filtrate is evaporated to dryness in vacuo. The residue is taken up in 250 ml of dichloromethane, washed twice with 250 ml of 2 N sodium hydroxide solution and then washed neutral with water, dried with sodium sulphate and evaporated to dryness in vacuo. Recrystallisation is carried out from diisopropyl ether/ethyl acetate.

Yield: 21.6 g (78.8 of theory)

Melting point: 104°-105° C. (colourless crystals)

Example II

2-[4-(Quinolin-2-yl-methoxy)phenyl]-2-cyclopentylacetonitrile

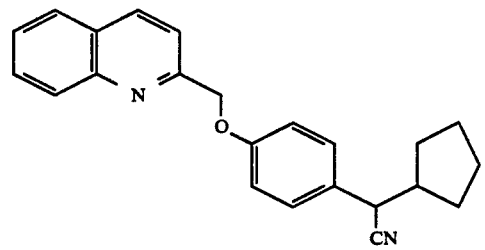

0.6 g (80 % pure) of sodium hydride (0.02 mol) is suspended in 40 ml of absolute DMF at 0° C., and 5.5 g (0.02 mol) of the compound from Example I in 20 ml of DMF are added dropwise. Evolution of hydrogen starts. During this process, the temperature rises to room temperature. The mixture is subsequently stirred at room temperature for a further hour and then cooled to 0° C., and 3 g (0.02 mol) of cyclopentyl bromide are added dropwise. The mixture is allowed to react further overnight and then concentrated to dryness in vacuo, and the residue is extracted by stirring with 180 ml of water/methylene chloride (1: 1) . The organic phase is separated off, dried and concentrated to a small volume, and the residue is separated by column chromatography (silica gel 60, mobile phase: toluene/ethyl acetate 9:1).

$R_f$=0.5

Yield: 4 g (53% of theory)

Melting point: 87° C. (colourless crystals)

Example III

2-[4-(Quinolin-2-yl-methoxy)phenyl]-2-cyclopentylacetamide

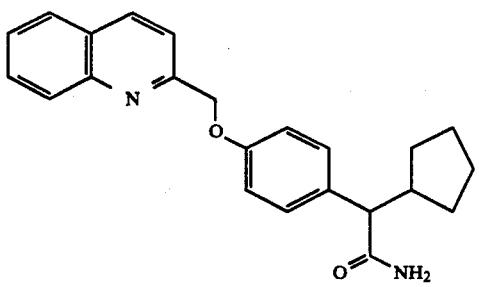

2 g (5.8 mmol) of the compound from Example II are suspended in 6 ml of concentrated hydrochloric acid, and the suspension is stirred at 40° C. overnight. After cooling to room temperature, THF is added until solution is complete, and the solution is neutralised with sodium bicarbonate solution. The organic phase is separated off, dried with sodium sulphate and concentrated to a small volume in vacuo. Separation is carried out by column chromatography (silica gel 60, mobile phase: dichloromethane/ethyl acetate/glacial acetic acid 80/15/15).

$R_f$=0.35 (the acid is at R, about 0.68)
Yield: 1.28 g (71.3 % of theory)
Melting point: 178° C. (colourless crystals)

PREPARATION EXAMPLES

Example 1

N-Acetyl-2-[4-(quinolin-2-yl-methoxy)phenyl]-2-cycloheptyl-acetamide

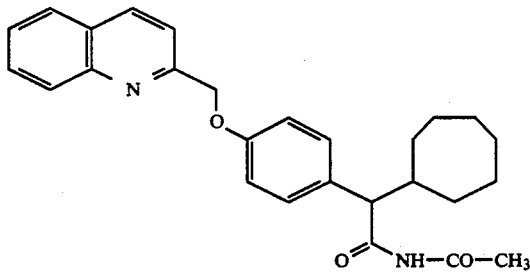

8.0 g (0.02 mol) of 2-[4-(quinolin-2-yl-methoxy)-phenyl]-2-cycloheptyl-acetic acid and 4.0 g (5.6 ml/0.04 mol) of triethylamine are dissolved in 80 ml of THF, the solution is cooled to 0° C., and 2.3 g (1.6 ml/0.02 mol) of mesyl chloride are added. 2.4 g (0.04 mol) of acetamide and 7.2 g (0.06 mol) of dimethylaminopyridine (DMAP), dissolved in 20 ml of THF, are added at 0° C. The mixture is allowed to react at room temperature for 48 hours (stirring) and is then concentrated to dryness in vacuo, and the residue is extracted by stirring with 50 ml of water and 50 ml of dichloromethane. The organic phase is separated off, dried and concentrated to a small volume, and the residue is separated by column chromatography (silica gel 60, mobile phase: toluene/ethyl acetate/ glacial acetic acid=8/1/1).

Yield: 0.8 g (9 % of theory)
Melting point: 148° C. (colourless crystals)

Example 2

N-Carbamoyl-2-[4-(quinolin-2-yl-methoxy)phenyl]-2-cycloheptyl-acetamide

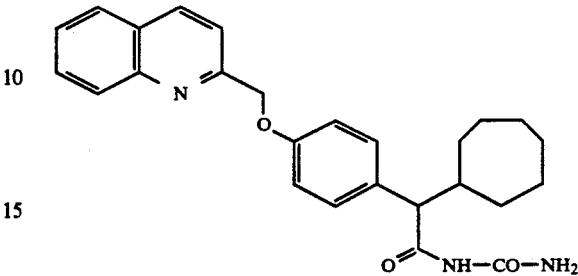

10 g (0.0257 mol) of the compound from Example III are suspended in 100 ml of THF at 0° C., and 2.5 ml (4 g/0.028 mol) of chlorosulphonyl isocyanate are added, with exclusion of moisture. The mixture is allowed to after-react for 15 minutes, while stirring, 120 ml of glacial acetic acid/water (2/1) are added and the temperature is allowed to rise to room temperature. To bring the reaction to completion, the mixture is heated at 100° C. for a further 15 minutes, during which a uniform solution forms. The solution is evaporated to dryness in vacuo, and the residue is extracted by stirring with 50 ml of water for 15 minutes and recrystallised from THF/ethylene chloride.

Yield: 8.0 g (72 % of theory)
Melting point: 222° C. (decomposition) (colourless crystals)

Examples 3 and 4

(+)—N-Carbamoyl-2-[4-(quinolin-2-yl-methoxy)-phenyl]-2-cycloheptyl-acetamide (3)

(−)—N-Carbamoyl-2-[4-(quinolin-2-yl-methoxy)-phenyl]-2-cycloheptyl-acetamide (4)

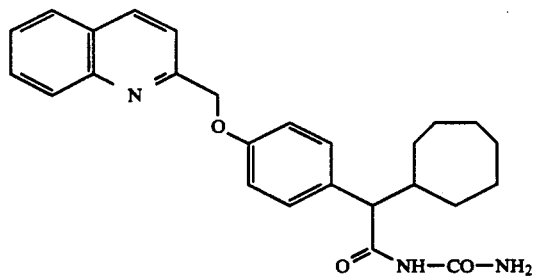

The (+)—and the (−)-enantismer are obtained analogously to the instructions of Example 2 by reaction of the enantiomerically pure (+)- or (−)-2-[4-(quinolin-2-ylmethoxy)phenyl]-2-cycloheptyl-acetamide with chlorosulphonyl isocyanate.

We claim:
1. Aquinolylmethoxyphenyl acetic acid acylamide or urea of the formula

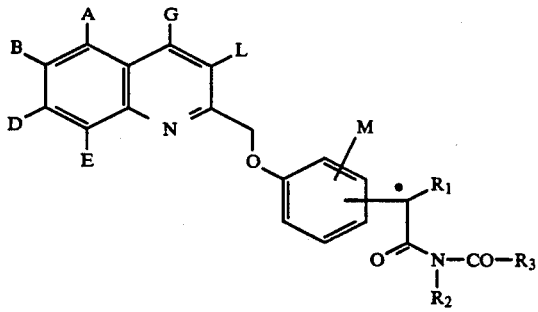

in which
- A, B, D, E, G, L and M independently of one another represent hydrogen, hydroxyl, halogen, cyano, carboxyl, nitro, trifluoromethyl or trifluoromethoxy, or represent straight-chain or branched alkyl or alkoxy having in each case up to 8 carbon atoms, or represent aryl having 6 to 10 carbon atoms, which is optionally substituted by halogen, hydroxyl, nitro or cyano,
- $R^1$ represents cycloalkyl having 3 to 12 carbon atoms, which is optionally substituted by straight-chain or branched alkyl having up to 8 carbon atoms,
- $R^2$ represents hydrogen, straight-chain or branched alkyl having up to 6 carbon atoms or benzyl and
- $R^3$ represents straight-chain or branched alkyl having up to 8 carbon atoms, benzyl, cycloalkyl having 3 to 12 carbon atoms or phenyl, which is optionally substituted by halogen, nitro, cyano or hydroxyl, or represents a group of the formula $-NR^4R^5$, wherein
  - $R^4$ and $R^5$ are identical or different and denote hydrogen, straight- chain or branched alkyl having up to 6 carbon atoms, benzyl or phenyl, or a physiologically acceptable salt thereof.

2. Aquinolylmethoxyphenylacetic acid acylamide or ureas according to claim 1, wherein
- A, B, C, D, E, G, L and M independently of one another represent hydrogen, hydroxyl, fluorine, chlorine, bromine, carboxyl, nitro, trifluoromethyl or trifluoromethoxy, or represent straight-chain or branched alkyl or alkoxy having in each case up to 6 carbon atoms, or represent phenyl, which is optionally substituted by fluorine, chlorine, bromine, hydroxyl, nitro or cyano,
- $R^1$ represents cyclopropyl, cyclobutyl, cyclopentyl, cyclohexyl, cycloheptyl or cyclooctyl, which are optionally substituted by straight-chain or branched alkyl having up to 6 carbon atoms,
- $R^2$ represents hydrogen or straight-chain or branched alkyl having up to 4 carbon atoms and
- $R^3$ represents straight-chain or branched alkyl having up to 6 carbon atoms, benzyl, cyclopropyl, cyclopentyl, cyclohexyl, cycloheptyl or phenyl, which is optionally substituted by fluorine, chlorine, bromine or hydroxyl, or represents a group of the formula $-NR^4R^5$, wherein
  - $R^4$ and $R^5$ are identical or different and denote hydrogen, straight-chain or branched alkyl having up to 4 carbon atoms or benzyl, or a physiologically acceptable salt thereof.

3. Aquinolylmethoxyphenyl acetic acid acylamidea or urea according to claim 1, wherein
- A, B, D, E, G, L and M independently of one another represent hydrogen, hydroxyl, fluorine, chlorine, bromine or straight-chain or branched alkyl having up to 4 carbon atoms,
- $R^1$ represents cyclopropyl cyclopentyl, cyclohexyl or cycloheptyl, which are optionally substituted by straight-chain or branched alkyl having up to 4 carbon atoms,
- $R^2$ represents hydrogen, methyl, ethyl or phenyl and
- $R^3$ represents straight-chain or branched alkyl having up to 4carbon atoms, cyclopropyl, cyclopentyl or cyclohexyl, or, represents a group of the formula $-NR^4R^5$, wherein
  - $R^4$ and $R^5$ are identical or different and denote hydrogen, methyl, ethyl or benzyl.

4. Aquinolylmethoxyphenylacetic acid acylamide or ureas according to claim 1, wherein A, B, D, E, G, L and M represent hydrogen.

5. A compound according to claim 1, wherein such compound is N-acetyl-2-[4-(quinolin-2-yl-methoxy)-phenyl]-2-cycloheptyl-acetamide of the formula

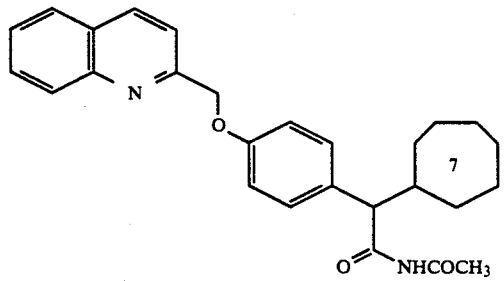

or a physiologically acceptable salt thereof.

6. A compound according to claim 1, wherein such compound is N-carbamoyl-2-[4-(quinolin-2-yl-methoxy)phenyl]-2-cycloheptyl-acetamide of the formula

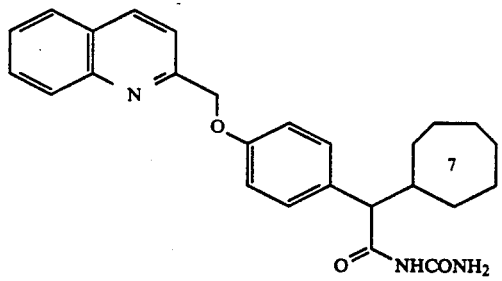

its (+)-enantiomer or (−)-enantiomer or a physiologically acceptable salt thereof.

7. A composition for inhibiting enzymatic reactions in the context of the arachidonic acid metabolism comprising an amount effective therefor of a compound or a salt thereof according to claim 1 and a pharmacologically acceptable diluent.

8. The method of inhibiting of the enzymatic reactions in the context of the arachidonic acid metabolism in a patient in need thereof which comprises administering to such patient an amount effective therefor of a compound or salt thereof according to claim 1.